(12) United States Patent
Ma et al.

(10) Patent No.: US 6,790,435 B1
(45) Date of Patent: Sep. 14, 2004

(54) ANTIPERSPIRANT COMPOSITIONS COMPRISING MICROEMULSIONS

(75) Inventors: Zhuning Ma, Chicago, IL (US); Richard Mark Brucks, Chicago, IL (US)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 35 days.

(21) Appl. No.: 10/089,648

(22) PCT Filed: Sep. 18, 2000

(86) PCT No.: PCT/EP00/09144

§ 371 (c)(1),
(2), (4) Date: Jul. 29, 2002

(87) PCT Pub. No.: WO01/24766

PCT Pub. Date: Apr. 12, 2001

Related U.S. Application Data

(60) Provisional application No. 60/157,382, filed on Oct. 1, 1999.

(51) Int. Cl.[7] .............................. A61K 7/32; A61K 7/34; A61K 7/38; A61K 7/00
(52) U.S. Cl. ............................. 424/65; 424/66; 424/68; 424/400; 424/401
(58) Field of Search .............................. 424/65, 66, 68, 424/400, 401

(56) References Cited

U.S. PATENT DOCUMENTS

| | | | | |
|---|---|---|---|---|
| 3,920,807 A | * | 11/1975 | Curry et al. ................... | 424/66 |
| 3,969,087 A | | 7/1976 | Saito et al. ...................... | 44/7 |
| 5,162,378 A | | 11/1992 | Guthauser ................... | 514/785 |
| 5,487,887 A | | 1/1996 | Benfatto ....................... | 424/66 |
| 5,575,990 A | | 11/1996 | Benfatto ....................... | 424/65 |
| 5,635,165 A | | 6/1997 | Panitch ......................... | 424/65 |
| 5,705,562 A | | 1/1998 | Hill ............................. | 524/731 |
| 5,707,613 A | | 1/1998 | Hill ......................... | 424/78.03 |
| 6,241,976 B1 | | 6/2001 | Esser et al. .................... | 424/65 |
| 6,248,312 B1 | | 6/2001 | Franklin et al. ............... | 424/65 |
| 6,287,544 B1 | | 9/2001 | Franklin et al. ............... | 424/65 |

FOREIGN PATENT DOCUMENTS

| | | |
|---|---|---|
| DE | 196 42 090 | 4/1998 |
| EP | 1 068 854 | 1/2001 |
| GB | 2 299 506 | 10/1996 |
| WO | 94/08610 | 4/1994 |
| WO | 94/19000 | 9/1994 |
| WO | 94/22420 | 10/1994 |
| WO | 98/27954 | 7/1998 |
| WO | 99/59537 | 11/1999 |
| WO | 00/61079 | 10/2000 |
| WO | 00/61096 | 10/2000 |

OTHER PUBLICATIONS

GB Search Report in a GB application GB 0109143.8.
Co–pending application: Brucks et al.; Ser. No.: 10/177,473; Filed: Apr. 5, 2002.
Derwent Abstract of EP 1 068 854—published Jan. 17, 2001.
Derwent Abstract of DE 196 42 090—published Apr. 9, 1998.

* cited by examiner

*Primary Examiner*—Shelley A. Dodson
(74) *Attorney, Agent, or Firm*—Kevin J. Stein

(57) ABSTRACT

Stable, clear, antiperspirant microemulsions containing cosmetic oils, antiperspirant salts, and water and combinations of cationic quaternary ammonium salt are provided. These microemulsions can be used in different types of applicators such as roll-on, sponge, mousse, pad, brush, gel and aerosol or non-aerosol spray applicators.

20 Claims, No Drawings

ANTIPERSPIRANT COMPOSITIONS COMPRISING MICROEMULSIONS

This application claims the benefit of Provisional application Ser. No. 60/157,382, filed Oct. 1, 1999.

FIELD OF THE INVENTION

This invention is related to microemulsions that contain cosmetically active ingredients. In a preferred embodiment, this invention is related to antiperspirant salt-containing microemulsions that are stable, clear liquids and are easy and inexpensive to produce.

BACKGROUND OF THE INVENTION

The microemulsions of the present invention contain water. Microemulsions of the present invention are transparent or translucent, optically isotropic and thermodynamically stable mixtures of oil and water stabilized by surfactants and perhaps co-surfactants. The particle size of the dispersed phase of a microemulsion is about 100 to about 2000 angstroms, more preferably are about 100 to about 1000 angstroms. They can form spontaneously or with a little energy. Therefore they are simple to prepare and are not process dependent i.e. the order of addition of starting materials or speed/type of mixing is not critical to the preparation of the microemulsions. It would be desirable to formulate antiperspirant compositions using microemulsions because microemulsions are easy and inexpensive to process and can be inherently clear without requiring refractive index matching of the aqueous and non-aqueous phases.

Microemulsions have attracted considerable technological and scientific interest. Water-in-oil (w/o) microemulsions containing water, an ionic surfactant, a cosurfactant and oil are the most investigated. The ionic surfactant—containing microemulsions usually exhibit stability over a large range of temperature. When inorganic salts are added, the minimum surfactant level to form water-in-oil microemulsions will increase. As the hydrocarbon oil chain length increases, the solubilization of aqueous phase into the oil phase decreases, while the liquid crystal area increases. Nonionic surfactant-containing water-in-oil microemulsions require a large amount of surfactant as well. Unfortunately, nonionic surfactant-containing microemulsions commonly exhibit a small temperature range of stability Microemulsions exist in the following forms: as water-in-oil, oil-in-water or as a bicontinuous phase, which is also called the surfactant phase. As used herein, the term "microemulsion means water-in-oil, oil-in-water or a bicontinuous phase, or mixtures thereof. Bicontinuous phase microemulsions are found to solubilize a high amount of water and oil with lower levels of surfactant. The region around a bicontinuous phase microemulsion may transition into a swollen lamellar phase, otherwise known as a liquid crystal phase, and in certain cases these phases (microemulsion and liquid crystal) may co-exist. These phases exhibit birefringence, shear induced (streaming) birefringence, and are thixotropic, viscoelastic and transparent. Because some of these systems exhibit increased viscosity the technical literature may refer to them as microemulsion gels.

It is an object of the present invention to provide antiperspirant compositions, which contain high levels of antiperspirant salts, cosmetic oils and surfactants suitable for application to the axilla. It is also an object of the present invention to provide antiperspirant compositions that do not require refractive index matching of the aqueous and non-aqueous phases in order to be clear. It is also an object of the present invention to provide microemulsion antipersprirant compositions that require little energy to manufacture. These and other objects of the present invention will become more readily apparent in the present application.

Patents and patent documents, which are cited in connection with the disclosed invention, are as follows:

DE 196 42 090 A1 discloses cosmetic or dermatologic compositions based on microemulsions.

U.S. Pat. No. 5,162,378 discloses water in oil microemulsions comprising cetyl dimethicone copolyol, water, silicone, alcohol, and 5–40% by weight of one or more salts.

U.S. Pat. No. 5,705,562 discloses a method of spontaneously forming a highly stable clear microemulsion by combining water, a volatile cyclic methyl siloxane or a volatile linear methyl siloxane and a silicone polyether surfactant. U.S. Pat. No. 5,707,613 is in the same patent family as the just mentioned patent.

WO 94/22420 is concerned with silicone-based skin care products, which are applied to the skin as aerosols and form a clear gel on the skin.

WO 94/19000 discloses pharmaceutical compositions in the form of a microemulsion which comprise and oil, a mixture of high and low HLB surfactants in which the high HLB surfactant comprises an aliphatic, aryl or aliphatic-aryl sulfate or sulfosuccinate or salt thereof, an aqueous phase and a biologically active agent.

WO 94/08610 discloses pharmaceutical compositions in the form of microemulsions which comprise an oil, a mixture of high and low HLB surfactants in which the high HLB surfactant comprises a medium-chain fatty acid salt, an aqueous phase and a biologically active agent.

U.S. Pat. No. 5,575,990 discloses roll-on antiperspirant compositions which are clear and, when applied to the human skin, do not leave a visible white residue after drying. The clear antiperspirant roll-on compositions are stable under varying temperature conditions and provide a suitable cosmetically acceptable feel or sensation when applied to the human skin.

U.S. Pat. No. 5,487,887 discloses roll-on antiperspirant compositions and more particularly concerns antiperspirant compositions which are clear and stable under varying temperature conditions and, when applied to the human skin, do not leave a visible white residue after drying. The compositions in the form of an oil-in-water microemulsion, comprise an antiperspirant active 5-30, PEG-7-glyceryl cocoate 5-25, emollients 0.5–3, cyclomethicone 3-7, and water 53–60%.

SUMMARY OF THE INVENTION

The invention relates to a composition in the form of a microemulsion comprising an antiperspirant salt, a cosmetic oil, and a combination of at least one cationic quaternary surfactant and at least one nonionic surfactant.

DETAILED DESCRIPTION OF THE INVENTION

The present invention is directed to antiperspirant salt-containing microemulsions that are stable and clear liquids, or clear antiperspirant gels.

Stable clear microemulsions containing cosmetic oils, antiperspirant salt, water, quaternary surfactants and non-ionic surfactants have been discovered. The microemulsions are primarily composed of bicontinous phase but the compositions include water-in-oil, oil-in-water, and microemulsion gels (liquid crystals). The microemulsions are novel antiperspirant compositions that can be used in different types of applicators such as roll-on, sponge, mousse, pad, wipe, brush, gel and aerosol or non-aerosol spray applicators.

The microemulsions discovered in this invention contain inorganic salts such as antiperspirant salts and cosmetic oils and the solubilization of high levels of both oil and aqueous solution of salts is achieved by incorporating combinations of a quaternary ammonium surfactant and a nonionic surfactant.

More specifically, the invention relates to a composition in the form of a microemulsion comprising an antiperspirant salt, cosmetic oils, and a combination of at least one cationic quaternary surfactant and at least one nonionic surfactant.

The invention also relates to a method for controlling or preventing underarm perspiration and malodor, which comprises applying to the underarm area a composition according to the invention.

The characteristics of the microemulsions of this invention include one or more of:

The microemulsions exhibit stability over a relatively large range of temperature.
The viscosity ranges from a thick gel to a low viscosity sprayable liquid.
The types of the microemulsions formed are dependent on the ratio of aqueous phase to the nonionic surfactant(s) and oil. When the percentage of the salt solution containing quaternary surfactant increases, the microemulsion changes from water-in-oil to oil-in-water type, and a bicontinuous microemulsion phase, or possibly a liquid crystal phase, will form in-between.
The microemulsions can contain a high level of inorganic salts.
The microemulsions contain a quaternary surfactant and a nonionic surfactant.
The microemulsions contain cosmetically acceptable oils.
A method for controlling or preventing underarm perspiration and malodor, which can be applied to the underarm area.
The application of the microemulsions can be accomplished by using various product dispensers.

As used herein % means weight percent unless otherwise specified.

As used herein the term cationic surfactant means quaternary ammonium surfactant.

The starting materials set forth herein are either known or can be prepared according to known methods. The compositions of the invention can be made by known methods or by methods that are analogous to known methods.

As used herein, microemulsions mean stable clear microemulsions containing cosmetic oil; antiperspirant salts, water and surfactants. The microemulsions described herein are primarily composed of bicontinuous phase but the compositions can include water-in-oil microemulsions. The compositions of the invention can also comprise a liquid crystal (that is, a microemulsion gel). More specifically, the compositions of the invention are selected from the group consisting of a microemulsion, a liquid crystal (that is, microemulsion gel), or a mixture of a microemulsion and a liquid crystal. The compositions of the invention comprise an antiperspirant salt, a cosmetic oil, and a combination of at least one cationic quaternary surfactant and at least one nonionic surfactant.

The compositions of the invention are novel antiperspirant compositions that can be used in different types of applicators such as roll-on, sponge, mousse, pad, brush, wipe, gel and aerosol or non-aerosol spray applicators.

All of the microemulsion compositions described contain antiperspirant salts and are clear and stable over a larger temperature range from room temperature to 45° C.–50° C. The viscosity of some of the water-in-oil microemulsions are less than 10 cst, therefore they are spray-able.

The invention relates to a composition in the form of a microemulsion comprising an antiperspirant salt, cosmetic oils, and a combination of at least one cationic quaternary surfactant and at least one nonionic surfactant.

A description of the ingredients included in the compositions of the invention now follows.

Antiperspirant Salts

Antiperspirant salts contained in these microemulsions include, but are not limited to, aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentachlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride or buffered aluminum sulfate.

Antiperspirant actives for use herein are often selected from astringent active salts, including in particular aluminum, zirconium and mixed aluminum/zirconium salts, including both inorganic salts, salts with organic anions and complexes. Preferred astringent salts include aluminum, zirconium and aluminum/zirconium halides and halohydrate salts, such as chlorohydrates.

Aluminum halohydrates are usually defined by the general formula $Al_2(OH)_xQ_y$ or a hydrate thereof in which Q represents chlorine, bromine or iodine, x is variable from 2 to 5 and x+y=6. The level of hydration is variable for example wherein there are up to about 6 or higher water molecules.

Zirconium actives can usually be represented by the empirical general formula: $ZrO(OH)_{2n-nz}B_z$ or a hydrate thereof in which z is a variable in the range of from 0.9 to 2.0 so that the value 2n–nz is zero or positive, n is the valence of B, and B is selected from the group consisting of chloride, other halide, sulphamate, sulfate and mixtures thereof. Possible hydration to a variable extent is represented by $wH_2O$. It is preferable that B represents chloride and the variable z lies in the range from 1.5 to 1.87. In practice, such zirconium salts are usually not employed by themselves, but as a component of a combined aluminum and zirconium-based antiperspirant. The level of hydration is variable for example wherein there are up to about 6 or higher water molecules.

The above aluminum and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminum chlorohydrate may be particularly preferred.

Antiperspirant complexes based on the above-mentioned astringent aluminum and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine, which has the formula $CH_2(NH_2)COOH$.

Complexes of a combination of aluminum halohydrates and zirconium chlorohydrates with or without with amino acids such as glycine can be employed in this invention. Certain of those Al/Zr-glycine complexes are commonly called ZAG in the literature. Aluminum-Zirconium actives or ZAG actives generally contain aluminum, zirconium and chloride with an Al/Zr ratio in a range from 2 to 10, especially 2 to 6, an Al/Cl ratio from 2.1 to 0.9. ZAG actives also contain a variable amount of glycine. In certain conditions, salts with an Al/Zr ratio greater than 2 (also known as low-zirconium actives) may be preferred. Actives of these preferred types are available from Westwood, from Summit and from Reheis.

Other antiperspirant-salt actives that may be utilized include astringent titanium salts, for example those describe in GB 2299506A.

The proportion of solid antiperspirant salt in a composition normally includes the weight of any water of hydration and any complexing agent that may also be present in the solid active. However, when the salt is in solution, its weight excludes any water present.

The antiperspirant active will often provide from 1 to 60% by weight of the aqueous phase, particularly from 10% to 60% of the aqueous phase. The final content of the salts in the formulations can range from 0.1% to 40% but 5–35% is preferred.

Other Aqueous Phase Ingredients

In addition to aluminum salts, the microemulsions, discovered in this invention, could solubilize aqueous solutions of monovalent, divalent and trivalent salts. The salts include sodium chloride, sodium sulfate, calcium chloride, calcium sulfate, magnesium chloride, aluminum sodium lactate, and mixtures thereof.

Other ingredients which can be dissolved in the aqueous phase include buffers, glycols, sugars, cyclodextrins, preservatives, antimicrobials, fragrances, chelating agents, amino acids, antimicrobials, anticholinergics, water-soluble polymers etc.

Water Content

The antiperspirant salts or other aqueous phase ingredients can be dissolved into water first and then combined with the non-aqueous phase. Water content in the final formulations can range from 1% to 60%, 5% to 30% is preferred and 10% to 25% is the most preferred.

Oil Phase

The oil phase of the compositions of the invention can contain cosmetic oils such as esters, ethers, long chain alcohols or ethoxylated alcohols, hydrocarbons, fatty acids, monoglycerides, diglycerides or triglycerides, fragrances, volatile or non-volatile silicone fluids. Cholesterol and some other lipids can be incorporated with the oil phase to act as emollients. The oil phase concentration can range from 0% to 95%, but 20% to 60% is preferred.

Silicone fluids that may be included in compositions of the invention include volatile and non-volatile silicone fluids such as cyclomethicones and dimethicones.

Non-volatile silicones such as phenyl tris(trimethylsiloxy) silane can be included in compositions of the invention.

Silicone elastomers such as DC 9040, or DC 9010 by Dow Corning or GE SFE 839 by General Electric, can be included in the compositions of the invention.

Esters selected from the group consisting of cetyl octanoate, C12-15 alcohol benzoate, isostearyl benzoate, diisopropyl adipate, isopropyl palmitate, isopropyl myristate and mixtures thereof may be included in the compositions of the invention.

Hydrocarbon oils such as aliphatic hydrocarbons (Permethyl 102A™, Permethyl 101™); hydrogenated polybutenes; hydrogenated polydecenes (Silkflo™); dioctylcyclohexane; mineral oil, cyclohexane and mixtures thereof may be included in the compositions of the invention.

Surfactants

Quaternary Ammonium Surfactants

Combinations of a cationic, quaternary ammonium surfactant(s) and a nonionic surfactant are employed in the compositions of the invention.

The quaternary surfactant in this invention is essential, without which the formulation will be either extremely sensitive to temperature or a microemulsion will not form. The preferred cationic surfactants employed in compositions of the invention are alkylamidopropyl alkyldimonium quaternaries.

The preferred cationic quaternary surfactants have the following structure:

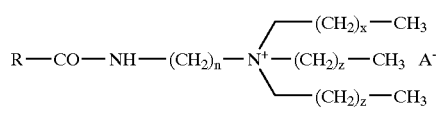

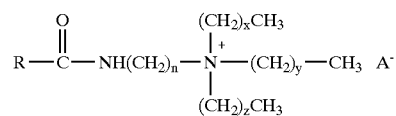

wherein n is one to six.

x is zero to three y is zero to three z is zero to three with the proviso that $x+y+z \leq 6$ A⁻ is any physiologically acceptable counter ion which does not adversely affect the composition, and more specifically A⁻ can be selected from the group consisting of chloride, bromide, ethosulfate, methyl sulfate, lactate, acetate, nitrate or sulfate.

where R is a ricinoleic derivative:

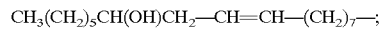

or mixtures thereof.

Obviously, variations on this structure, known to the art, can also be incorporated into embodiments of this invention. The variations on surfactant structure should exhibit solubility in the aqueous antiperspirant salt solution. If the above mentioned solubility is maintained then variations in the quaternary ammonium salts can include but are not limited to, increasing or decreasing the alkyl chain length, changing the position or removal of the hydroxyl group, changing the position or removing completely the double bond or combinations thereof.

The most preferred quaternary surfactant is ricinoleamidopropyl ethyldimonium ethosulfate a compound according to the formula above wherein n=3, x=1, y=0, z=0, A$^-$=ethosulfate and

$R=CH_3(CH_2)_5CH(OH)CH_2-CH=CH-(CH_2)_7-$.

The surfactant described just above is also known, under the following trade names, as Surfactol Q4 from CasChem Inc., Lipoquat R from Lipo Chemicals or Mackernium DC-159 from McIntyre Chemical. Preferably the quaternary surfactant is supplied in a concentrated form (>90% active) with a low free amine content. This form is readily miscible with the aqueous antiperspirant-salt solution.

The quaternary surfactant(s) in the compositions of the invention range from 0.1% to 30%, where 2% to 15% is preferred.

Nonionic Surfactants

The nonionic surfactant or co-surfactants employed in the compositions of the invention can be polyethoxylated alcohol ethers or esters, polyglycerol mono or di-esters, glyceryl esters or branched guerbet ethoxylates or alcohols, or long chain carboxylic acids or combinations thereof. These compounds have a hydrophilic-lipophilic balance of between about 2 to about 15 and preferably less than about 12. Non-limiting examples are polyglycerol-3 diisostearate; glycerol oleate; poly glycerol-2 monoisostearate; polyglycerol-2 diisostearate, glyceryl isostearate. The most preferred ones are polyglyceryl-3 diisostearate, glyceryl isosterate and glycerol oleate or combinations thereof.

The ratio of cationic surfactant to aqueous phase containing antiperspirant salt ranges from 30/70 to 4/96, the ratio from 10/90 to 5/95 is preferred. The ratio of aqueous phase including salts, water and cationic surfactant to nonionic surfactant is 90/10 to 70/30, and the ratio from 90/10 to 80/20 is preferred.

FORMULATION EXAMPLES

The following samples are stable for one month at room temperature. The particle size or domain length of these compositions are between about 150 to about 600 angstroms. All samples are clear. Some samples exhibit streaming birefringence. Some samples exhibit birefringence. The viscosity of these samples range from a thin liquid to a gel. These microemulsions are primarily composed of bicontinuous phase but the compositions include water-in-oil, and microemulsion gels (liquid crystals).

The following formulation examples are illustrative of the invention.

The following is a general formula for an antiperspirant microemulsion of the present invention.

General Formulation Example:

| Components | | Specific Examples of components | Range | Preferred range |
|---|---|---|---|---|
| Oil Phase* | | Aliphatic Hydrocarbon 90–10% | 0–95% | 20–60% |
| | | Volatile Silicone 10–90% | | |
| Aqueous Phase* | Water | Deionized Water | 1–60% | 5–30% |
| | Antiperspirant-Salt | ACH or AZG or other salts | 0.1–40% | 5–35% |
| Non-ionic surfactant | | Polyglycerol-3 diisosterate | 0.2 to 30% | 4–15% |
| | | | | 5–10% most preferred |
| Cationic Quaternary Ammonium Surfactant | | Ricinoleamidopropyl ethyl dimonium ethosulfate | 0.1–30% | 2–15% |

*Cosmetic additives or other optional ingredients can be added to either phase as required.

Generalized manufacturing procedure:

1. Weigh all the oil phase components into a suitable vessel and mix until homogenous. Heat may be used to expedite dispersion of components solid at room temperature.
2. The aqueous phase is prepared by mixing the quaternary ammonium surfactant with the antiperspirant salt solution.
3. Add the oil and water phases together and mix until a clear, homogenous dispersion is formed.
4. The microemulsion formulation is transferred into a suitable dispenser or applicator.

The following examples more fully illustrate embodiments of this invention, all percentages being by weight unless otherwise noted. The following specific examples, which are compositions of the invention, were made.

Compositions were prepared according to the following procedure:

1. Mix the cationic surfactant with the antiperspirant salt solution
2. Mix the nonionic surfactant with the oil mixture, then add the two mixtures together and mix well.
3. Heat may be applied to better dissolve solid nonionic surfactants, which are solid such as glyceryl oleate, in the oil phase prior to mixing the aqueous and non-aqueous phases

|    | Prisorine 3700 % | Cationic** % | Aluminum Zirconium tetra % | Water % | DC 245 % | HC* % | |
|----|------------------|--------------|----------------------------|---------|----------|-------|---|
| 1  | 10.03 | 5.98 | 13.55 | 20.31 | 15.04 | 35.09 | |
| 2  | 8.99  | 4.66 | 10.57 | 15.85 | 17.98 | 41.95 | |
| 3  | 7.02  | 3.45 | 7.82  | 11.74 | 20.99 | 48.98 | |
| 4  | 3.97  | 1.73 | 3.93  | 5.91  | 25.34 | 59.12 | |

|    | Prisorine 3700 % | Cationic** % | ACH % | Water % | DC 245 % | HC* % | |
|----|------------------|--------------|-------|---------|----------|-------|---|
| 6  | 9.97 | 6.78 | 19.2 | 19.2 | 13.45 | 31.40 | |
| 7  | 2.99 | 1.02 | 2.89 | 2.90 | 27.06 | 63.14 | |

|    | Glyceryl oleate % | Cationic** % | Aluminum Zirconium tetra % | Water % | DC 245 % | HC* % | |
|----|-------------------|--------------|----------------------------|---------|----------|-------|---|
| 8  | 14.24 | 11.71 | 22.09 | 33.13 | 5.65  | 13.18 | |
| 9  | 11.05 | 8.55  | 16.13 | 24.20 | 12.02 | 28.05 | |
| 10 | 10.02 | 7.89  | 14.88 | 22.33 | 13.46 | 31.42 | |
| 11 | 9.99  | 6.98  | 13.17 | 19.75 | 15.03 | 35.08 | Birefringent |
| 12 | 14.95 | 12.27 | 23.13 | 34.69 | 4.49  | 10.47 | |

|    | Glyceryl oleate % | Cationic** % | ACH % | Water % | DC 245 % | HC* % | |
|----|-------------------|--------------|-------|---------|----------|-------|---|
| 13 | 3.99 | 12.91 | 36.57 | 36.57 | 2.99  | 6.97  | |
| 14 | 2.99 | 1.83  | 5.17  | 5.18  | 25.45 | 59.38 | Birefringent |
| 15 | 8.50 | 7.70  | 21.82 | 21.82 | 12.05 | 28.11 | |

|    | Prisorine 3700 % | Cationic** % | Aluminum Zirconium penta % | Water % | DC 245 % | HC* % | |
|----|------------------|--------------|----------------------------|---------|----------|-------|---|
| 16 | 16.64 | 8.67 | 23.2  | 34.8  | 5.01  | 11.68 | Birefringent |
| 17 | 14.12 | 6.04 | 16.17 | 24.25 | 11.83 | 27.59 | Birefringent |
| 18 | 7.46  | 4.87 | 16.30 | 16.29 | 16.52 | 38.56 | |

|    | Glyceryl isostearate % | Cationic** % | Aluminum Zirconium penta % | Water % | DC 245 % | HC* % | |
|----|------------------------|--------------|----------------------------|---------|----------|-------|---|
| 19 | 11.02 | 11.09 | 25.15 | 37.72 | 4.51  | 10.51 | Birefringent |
| 20 | 10.02 | 8.99  | 20.37 | 30.55 | 9.02  | 21.05 | Birefringent |
| 21 | 9.03  | 7.64  | 17.32 | 25.99 | 12.00 | 28.02 | Birefringent |
| 22 | 7.97  | 6.32  | 14.32 | 21.47 | 14.98 | 34.94 | |
| 23 | 6.02  | 3.60  | 8.15  | 12.22 | 21.00 | 49.01 | |
| 24 | 6.02  | 4.434 | 7.82  | 11.72 | 21.00 | 49.01 | |
| 25 | 8.52  | 13.64 | 24.03 | 36.05 | 5.33  | 12.43 | |
| 26 | 9.00  | 5.71  | 8.72  | 16.46 | 18.03 | 42.08 | |
| 26 | 4.68  | 0.14  | 0.25  | 0.38  | 28.36 | 66.19 | |
| 27 | 9.74  | 0.46  | 0.81  | 1.21  | 26.33 | 61.45 | |
| 28 | 11.47 | 11.80 | 26.76 | 40.13 | 2.95  | 6.89  | Birefringent |
| 29 | 11.11 | 11.07 | 25.10 | 37.65 | 4.52  | 10.55 | |
| 30 | 10.03 | 6.74  | 15.29 | 22.93 | 13.50 | 31.51 | |
| 31 | 9.54  | 6.06  | 13.73 | 20.60 | 15.02 | 35.05 | |
| 32 | 11.38 | 11.91 | 27.00 | 40.51 | 2.76  | 6.44  | |

|    | Glyceryl isostearate % | Cationic** % | Aluminum Zirconium penta % | Water % | DC 245 % | Silkoflo 366-NF % | |
|----|------------------------|--------------|----------------------------|---------|----------|--------------------|---|
| 33 | 7.45  | 16.94 | 30.34 | 44.66 | 0.43  | 0.18  | Birefringent |
| 34 | 12.36 | 11.88 | 22.40 | 33.59 | 13.85 | 5.92  | Birefringent |
| 35 | 12.06 | 11.92 | 22.47 | 33.71 | 13.89 | 5.95  | |
| 36 | 12.05 | 9.26  | 17.46 | 26.19 | 24.53 | 10.51 | |
| 37 | 10.93 | 7.78  | 14.67 | 22.01 | 31.23 | 13.38 | |

|    | Prisorine 3700 % | Cationic** % | Aluminum Zirconium penta % | Water % | DC 245 % | Silkflo 366-NF % | |
|----|------------------|--------------|----------------------------|---------|----------|-------------------|---|
| 38 | 10.67 | 11.19 | 25.36 | 38.05 | 10.31 | 4.42  | Birefringent |
| 39 | 14.01 | 9.89  | 22.41 | 33.61 | 14.06 | 6.02  | |
| 40 | 4.93  | 2.22  | 5.03  | 7.55  | 56.20 | 24.07 | |
| 41 | 13.98 | 6.90  | 15.64 | 23.45 | 28.02 | 12.01 | |
| 42 | 11.51 | 5.77  | 13.08 | 19.62 | 35.02 | 15.00 | |
| 43 | 9.51  | 4.58  | 10.37 | 15.56 | 41.98 | 18.00 | |
| 44 | 7.98  | 3.32  | 7.52  | 11.28 | 48.93 | 20.97 | |
| 45 | 11.05 | 13.48 | 25.42 | 38.08 | 8.34  | 3.63  | |
| 46 | 12.03 | 11.91 | 22.46 | 33.70 | 13.92 | 5.98  | |

-continued

| | | | | | | | |
|---|---|---|---|---|---|---|---|
| 47 | 11.96 | 9.80 | 18.49 | 27.73 | 22.41 | 9.61 | Birefringent |
| 48 | 15.96 | 11.22 | 21.16 | 31.73 | 13.95 | 5.98 | Birefringent |
| 49 | 14.03 | 9.78 | 18.44 | 27.66 | 21.06 | 9.03 | |

| | Isofol 12 alcohol ethoxylate/ cholesterol | Cationic** % | ACH % | Water % | DC 245 % | HC* % | |
|---|---|---|---|---|---|---|---|
| 50 | 20.15/0 | 8.21 | 23.26 | 23.26 | 7.52 | 17.60 | Birefringent |
| 51 | 12.71/2.44 | 6.72 | 18.85 | 18.85 | 12.12 | 28.31 | |

*HC means hydrocarbon: Permethyl 102A, listed in the above table
**Cationic means the cationic surfactant: Ricinoleamidopropyl ethyldimonium ethosulphate
Further examples include:

Example 52

| Ingredient (INCI) | Trade Names | Source | Percent |
|---|---|---|---|
| Ricinoleamidopropyl Dimonium Ethosulfate | Surfactol Q4 | CasChem, Inc | 7.50% |
| Polyglycerol-3 Diisostearate | Prisorine PG3 DI 3700 | Uniqema | 10% |
| Aliphatic Hydrocarbon | Permethyl 102A | Presperse | 28% |
| Cyclopentasiloxane | DC245 | Dow Corning | 12% |
| Aluminum Chlorohydrate 50% | Westchlor 200 | Westwood | 42.50% |
| | | Total: | 100% |

Example 53

| Ingredient (INCI) | Trade Names | Source | Percent |
|---|---|---|---|
| Ricinoleamidopropyl Dimonium Ethosulfate | Surfactol Q4 | CasChem, Inc | 7.50% |
| Glyceryl Isostearate | Peceol Iso-stearique | Gattefosse | 10% |
| Hydrogenated Polydecene | Silkfo 366 | Lipo Chemicals | 12% |
| Cyclopentasiloxane | DC245 | Dow Corning | 28% |
| Aluminum Zirconium Pentachlorohydrate 40% | Low Zirconium Penta Solution R280-130 | Reheis | 42.50% |
| | | Total: | 100% |

Example 54

| Ingredient (INCI) | Trade Names | Source | Percent |
|---|---|---|---|
| Ricinoleamidopropyl Dimonium Ethosulfate | Surfactol Q4 | CasChem, Inc | 2.77% |
| Aluminum Zirconium Pentachlorohydrate 40% | Low Zirconium Penta Solution R280-130 | Reheis | 47.63% |
| Glyceryl Isostearate | Peceol Iso-stearique | Gattefosse | 3.06% |
| Hydrogenated Polydecene | Silkflo 366 | Lipo Chemicals | 11.70% |
| Cyclopentasiloxane | DC245 | Dow Corning | 27.04% |
| Ethoxylated Guerbet Alcohol C14/4 EO HLB ~9 | Novel II Isofol 14T+4EO | Condea Vista | 7.80% |
| | | Total: | 100% |

Examples 55 and 56

| Ingredient (INCI) | Trade Names | Supplier | 55 Percent | 56 Percent |
|---|---|---|---|---|
| Ricinoleamidopropyl ethyl dimonium ethosulfate | Surfactol Q4 | Caschem | 2.32 | 2.83 |
| Aluminum zirconium penta chlorohydrate | Rezal 67 | Reheis | 15.94 | 18.13 |
| Water | Deionized Water | Stock | 23.91 | 27.19 |
| Urea | Urea | Janssen Chimica | — | 3.34 |
| Cyclopentasiloxane | DC 245 | Dow Corning | 29.08 | 22.08 |
| Polydecene hydrogenated | Silkflo 336NF | Lipo Chemicals | 11.62 | 9.46 |
| Glyceryl isostearate | Peceol isostearique | Gattefosse | 5.26 | — |
| Polyglyceryl-3 diisostearate | Prisorine 3700 | Unichema | 0.87 | 3.49 |
| Ethoxylated Guerbet alcohol $C_{18}EO_{10}$ | Novel II I18T-10 ethoxylate | Condea Vista | 3.36 | 6.19 |
| 2-hexyldecanol (Guerbet C16 Alcohol) | Isoflo 16 | Condea Vista | 7.64 | 7.29 |
| | | Total | 100 | 100 |

Raw materials used in preparation of the example compositions of the invention are as follows:

| Trade Name | Chemical Name | Vender |
|---|---|---|
| DC 245 | Cyclomethicone D5 | Dow Corning |
| DC 344 | Cyclomethicone D4 | Dow Corning |
| Silkflo 364 or 366 | Hydrogenated Polydecene | Lipo Chemical |
| Permethyl 102 A | Aliphatic hydrocarbon | Permethyl Specialties |
| Permethyl 101 | Aliphatic hydrocarbon | Permethyl Specialties |
| Trivent OC-16 | Cetyl octanoate | Trivent Chemical Company |
| Cetiol S | Dioctyl cyclohexane | Henkel Corporation |
| Peceol Isostearique | Glyceryl isostearate | Gattefosse |
| Monomuls 90-018 | Glycerol oleate | Henkel Corporation |
| Fancol Polyiso 275 | Hydrogenated polyisobutene | The Fanning Corp. |
| Finsolve TN | C12–C15 alcohol benzoate | Finetex |
| Finsolve SB | Isostearyl benzoate | Finetex |
| Prisorine 3700 | Polyglycerol-3 Diisostearate | Unichema North America |
| Prisorine 3792 | Polyglycerol-2 diisostearate | Unichema North America |
| Prisorine 3791 | Polyglycerol-2 monoisostearate | Unichema North America |

-continued

| Trade Name | Chemical Name | Vender |
| --- | --- | --- |
| Glucate DO | Methyl glucoside dioleate | Amercol |
| Glucate SS | Methyl glucoside sesqui-stearate | Amercol |
| Estol 3609 | Glycerol tri-2-ethyl-hexanoate | Unichema North America |
| Dow Corning 556 | Phenyl tris(trimethyl-siloxy)silane | Dow Corning |
| Ceraphyl 230 | Diisopropyl Adipate | ISP Van Dyk Inc |
| Mineral oil | Hydrocarbon | Witco |
| Novel II 12-5 Ethoxy-late | Ethoxylated alcohol or Branched Guerbent ethoxylate | Condea Vista Company |
| Cholesterol | Cholesterol | Rita Corporation |
| Surfactol Q4 | Ricinoleamidopropyl dimonium sulfate | CasChem |
| Westchlor 200 50% w/w | Alminum chlorohydrate (ACH) | West Wood |
| Low zirconium penta solution R280-130 40% w/w | Low zirconium: Aluminum Zirconium Pentachlorohydrate | Reheis |
| Rezal 67 Solution 40% w/w | Aluminum Zirconium Pentachlorohydrate (penta) | Reheis |
| Westchlor Zr 44 50% w/w | Aluminum Zirconium tetrachlorohydrate (tetra) | West Wood |
| Westchlor Zr 41 45% w/w | Aluminum Zirconium tetrachlorohydrexglycine | West Wood |

The foregoing description and examples illustrate selected embodiments of the present invention. In light thereof, various modifications would be suggested to one skilled in the art, all of which are within the spirit and scope of this invention.

What is claimed is:

1. A composition which is selected from the group consisting of a microemulsion, a liquid crystal, or a mixture of a microemulsion and a liquid crystal which comprises an antiperspirant salt, a cosmetic oil, and a combination of at least one cationic quaternary surfactant and at least one nonionic surfactant.

2. A composition in accordance with claim 1 wherein said antiperspirant salt is selected from the group consisting of aluminum, zirconium and mixed aluminum/zirconium salts.

3. A composition in accordance with claim 1 wherein said antiperspirant salt is a zirconium salt complexed with aluminum salts having coordinated or bound water.

4. A composition in accordance with claim 1 wherein said antiperspirant salt is present in the aqueous phase at from about 10% to about 60%.

5. A composition in accordance with claim 4 wherein said antiperspirant salt is present in the aqueous phase at from 10% to about 60%.

6. A composition in accordance with claim 1 wherein said aqueous phase further comprises a buffer, a glycol, a sugar, a cyclodextrin, a preservative, an antimicrobial, a chelating agent, a water-soluble polymer, an anticholinergic, a monovalent salt, a divalent salt, a trivalent salt, fragrances or mixtures thereof.

7. A composition in accordance with claim 1 wherein said aqueous phase is present at about 1% to about 60%.

8. A composition in accordance with claim 1 said cosmetic oil comprises esters, ethers, long chain alcohols, or ethoxylated alcohols, hydrocarbons, fatty acids, monoglycerides, diglycerides triglycerides, fragrances and volatile or non-volatile silicone fluids, and cholesterol.

9. A composition in accordance with claim 8 wherein said oil phase comprises silicone fluids which in turn comprise a volatile or non-volatile silicone such as cyclomethicone or dimethicone.

10. A composition in accordance with claim 8 wherein said non-volatile silicone is phenyl tris(trimethylsiloxy) silane.

11. A composition in accordance with claim 8 wherein said esters are selected from the group consisting of cetyl octanoate, C12-15 alcohol benzoate, isostearyl benzoate, diisopropyl adipate and mixtures thereof.

12. A composition in accordance with claim 8 wherein said hydrocarbon fluids are selected from the group such as aliphatic hydrocarbons; hydrogenated polydecenes; hydrogenated polybutenes; dioctylcyclohexane; mineral oil, cyclohexane and mixtures thereof.

13. A composition in accordance with claim 1 wherein the cationic quaternary ammonium surfactant has the following structure:

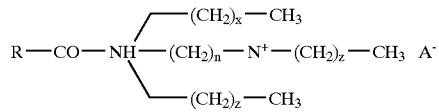

wherein n is one to six x is zero to three y is zero to three z is zero to three with the proviso that $x+y+z \leq 6$ $A^-$ is any physiologically acceptable counter ion which does not adversely affect the composition, and more specifically $A^-$ can be selected from the group consisting of chloride, bromide, ethosulfate, methyl sulfate, lactate, acetate, nitrate or sulfate, Where R is a ricinoleic derivative:

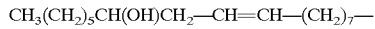

or mixtures thereof.

14. A composition in accordance with claim 13 wherein n=3, x=1, y=0, z=0, $A^-$=ethosulfate and R=$CH_3$—$(CH_2)_5$—CH(OH)—$CH_2$—CH=CH—$(CH_2)_7$—.

15. A composition in accordance with claim 13 wherein said cationic quaternary ammonium surfactant is present at 0.1% to 30%.

16. A method for controlling or preventing underarm perspiration and malodor which comprises applying, to an underarm, an effective amount of a composition of claim 1.

17. A composition in accordance with claim 1 wherein said aqueous phase is present at about 5% to about 30%.

18. A composition in accordance with claim 1 wherein said aqueous phase is present at about 10% to about 25%.

19. A composition in accordance with claim 13 wherein said cationic quaternary ammonium surfactant is present at about 1% to about 30%.

20. A composition in accordance with claim 13 wherein said cationic quaternary ammonium surfactant is present at about 2% to about 15%.

* * * * *